United States Patent [19]

Kamiyama et al.

[11] 4,447,328
[45] May 8, 1984

[54] FILLER FOR LIQUID CHROMATOGRAPHY AND METHOD FOR SEPARATING WATER-SOLUBLE SUBSTANCES USING SAID FILLER

[75] Inventors: Fumio Kamiyama, Kyoto; Kazutoshi Yamazaki, Ohtsu; Minoru Kohara, Kyoto; Mituo Nagata, Shiga, all of Japan

[73] Assignee: Sekisu Kagaku Kogyo Kabushiki Kaisha, Osaka, Japan

[21] Appl. No.: 349,252

[22] Filed: Feb. 16, 1982

Related U.S. Application Data

[63] Continuation of Ser. No. 160,741, Jun. 18, 1980, abandoned.

[30] Foreign Application Priority Data

Jun. 22, 1979 [JP] Japan .................................. 54-79494
Aug. 6, 1979 [JP] Japan .................................. 54-100363

[51] Int. Cl.³ ............................................. B01D 15/08
[52] U.S. Cl. ...................................... 210/635; 210/656
[58] Field of Search ....................... 210/635, 656, 198.2

[56] References Cited

U.S. PATENT DOCUMENTS

| | | | |
|---|---|---|---|
| 3,322,695 | 9/1967 | Alfaet et al. | 260/141 X |
| 3,326,875 | 6/1967 | Moore et al. | 210/656 |
| 3,657,117 | 4/1972 | Pfitznea et al. | 210/635 |
| 3,960,720 | 6/1976 | Porath et al. | 210/198.2 |
| 4,133,753 | 1/1979 | Takeuchi et al. | 210/656 |
| 4,135,892 | 1/1979 | Coupek et al. | 55/386 X |
| 4,140,653 | 2/1979 | Imura et al. | 210/198.2 |
| 4,189,370 | 2/1980 | Boschetti | 210/198.2 |

FOREIGN PATENT DOCUMENTS 50-1760  1/1975  Japan .

OTHER PUBLICATIONS

High Performance Liquid Chromatography by Knox, Edinburg University Press Scotland, pp. 45–50, 1978.
Introduction to Modern Liquid Chromatography by Snyder & Kirkland, John Wiley & Sons of New York, pp. 2,3,85–89 and 200–202 & 209, 1974.

Primary Examiner—John Adee
Attorney, Agent, or Firm—Wenderoth, Lind & Ponack

[57] ABSTRACT

A liquid-chromatographic filler comprising a particulate synthetic polymer, such as glycerol di or tri (meth) acrylate wherein the filler exhibits a behavior such that in chromatography using polyethylene glycol as a sample and water as an eluent, the elution time of the sample increases with a rise in temperature. Separation of water-soluble substances by liquid chromatography can be achieved by using an aqueous medium as an eluent, and this filler.

5 Claims, 3 Drawing Figures

FILLER FOR LIQUID CHROMATOGRAPHY AND METHOD FOR SEPARATING WATER-SOLUBLE SUBSTANCES USING SAID FILLER

This application is a contination of Ser. No. 160,741, filed June 18, 1980, now abandoned.

This invention relates to a filler for use in liquid chromatography, particularly a filler useful for liquid chromatography of hydrophilic substances, and to a method for separating water-soluble substances using said filler.

Conventional liquid-chromatographic fillers for separation of hydrophilic substances are classified by their separating mechanisms into gel-permeation chromatographic fillers, reversed phase chromatographic fillers, ion exchange chromatographic fillers, etc. The fillers for gel-permeation chromatography have pores inside, and operate by the separating mechanism whereby a delay is caused in elution time by the diffusing of a sample in the pores and separation is effected by differences in the delay of time. Ion exchange chromatography has the mechanism that a delay in elution time is caused by the electrostatic interaction between the surface of a fixed phase having a dissociable substituent and a sample having a charge opposite to the fixed phase surface. In reversed phase chromatography, a sample is held on a fixed phase by the interaction of the hydrophobic surface of the fixed phase and hydrophobic groups of the sample, and therefore a sample having greater hydrophobicity requires a longer elution time.

Several types of these chromatographic fillers are now commercially available. Many of these known fillers, however, have hydrophobicity, and cannot permit use of water free from an organic solvent as an eluent. Hence, these fillers are unsuitable for separation of hydrophilic substances.

A silica gel carrier having long-chain alkyl groups chemically bound thereto is known as a filler in liquid chromatography for separation of hydrophilic substances. In this filler, the interaction of a sample and the alkyl groups based on their hydrophobicity, i.e. the action of prolonging the elution time of a non-polar substance, and the action of adsorption between the sample and a silanol group, i.e. the action of prolonging the elution time of a polar substance, are simultaneously performed. It is difficult therefore to anticipate the behavior of the filler in separating the individual components of the sample. Furthermore, when water alone is used as an eluent, the separating ability of the filler decreases, and the individual components are difficult to separate. Accordingly, this modified silica gel carrier does not have sufficient properties for separation of biochemical substances such as proteins.

Thus, no liquid-chromatographic filler has been provided to date which has high performance in separating hydrophilic substances, especially biochemical substances.

It is an object of this invention therefore to provide a liquid-chromatographic filler which is effective for separation of hydrophilic substances with good accuracy using water alone as an eluent.

According to this invention, there is provided a liquid-chromatographic filler comprising a particulate synthetic polymer, said filler exhibiting such a behavior that in chromatography using polyethylene glycol as a sample and water as an eluent, the elution time of the sample increases with a rise in temperature.

The present invention also provides a liquid chromatographic filler comprising a particulate-synthetic polymer and having the property described above, in which the polymer has both a non-dissociable hydrophilic group and a hydrophobic group.

It is essential that the synthetic polymer constituting the liquid-chromatographic filler exhibits such a behavior that in liquid chromatography using polyethylene glycol as a sample and water as an eluent, the elution time of the sample increases with a rise in temperature. In other words, the synthetic polymer is firstly required to be usable as a filler in chromatography involving use of water as an eluent. Secondly, when it is used as a filler in chromatography involving use of polyethylene glycol as a sample and water as an eluent, it should prolong the elution time of the sample with a rise in temperature. The second requirement means that the synthetic polymer is a filler for liquid chromatography whose separating mechanism is hydrophobic interaction. For example, when liquid chromatography is carried out on a column packed with the filler of this invention using polyethylene glycol having a degree of polymerization of 10 as a sample, it is preferred that the elution time of the sample at a column temperature of 50° C. should be at least 10 seconds longer than that at a temperature of 20° C. With conventional fillers, the elution time usually becomes shorter with a rise in temperature. For example, with the aforesaid modified silica gel filler comprising silica gel and long-chain alkyl groups chemically bound thereto, the elution time decreases with a rise in temperature because both the hydrophobic interaction based on the alkyl groups and the adsorbing action of the silanol groups are simultaneously performed. The separating action of the filler of this invention is based mainly on hydrophobic interaction, and a liquid-chromatographic filler having both this property and the aforesaid first requirement (i.e., usability in chromatography involving use of water as an eluent) is novel. No filler has been known to date which exhibits the aforesaid behavior in reversed phase chromatography using water as an eluent. The "hydrophobic interaction", as referred to herein, is not an interaction intended mainly for securing stabilization by an energy of bonding such as an electrostatic bond or hydrogen bond, but is a statistical thermodynamic interaction resulting mainly in an increase in entropy.

Since the filler of this invention has the aforesaid properties, it is effective for separation of hydrophilic substances, especially biochemical substances such as proteins, amino acids and enzymes.

The separating temperature for chromatography using the filler of this invention is one which is suitable when water is used as an eluent, usually from 0° C. to 85° C.

It has been found that in order for a filler to permit use of water as an eluent, a synthetic polymer constituting the filler should have hydrophilic groups having affinity for water, thereby enabling the surface of the filler to be wetted with water. Those hydrophilic groups which are dissociable, such as carboxyl and amino groups, have an effect of imparting hydrophilicity, but the presence of such dissociable groups in the filler causes an ion-exchange mechanism to be in operation and complicates the separating behavior of the filler in chromatography. Furthermore, inorganic hydrophilic groups typified by a silanol group complicates the separating behavior of the filler in chromatography because of the action of a strong adsorbing mechanism.

Accordingly, these dissociable substituents or inorganic hydrophilic groups have been found to be unsuitable. It has been found that non-dissociable organic hydrophilic groups capable of imparting hydrophilicity without operation of an ion exchange mechanism or adsorbing mechanism are suitable. Such non-dissociable hydrophilic groups include, for example, alcoholic hydroxyl, amide, oxyalkylene and ester groups.

Prolongation of the elution time of a sample with a rise in temperature shows that the separating action of the filler is mostly based on hydrophobic interaction. In order to induce such an interaction, it is necessary that hydrophobic groups such as alkyl, phenyl and alkylene groups be present in the synthetic polymer constituting the filler.

Thus, the synthetic polymer constituting the filler of this invention should at least contain both a non-dissociable hydrophilic group and a hydrophobic group in the molecule. Such a synthetic polymer can be obtained by polymerizing a monomer having a non-dissociable hydrophilic group and a hydrophobic group in the molecule.

Examples of such a monomer are given below.

1. Polyfunctional monomers having ester groups:
Tetramethylolmethane tetraacrylate,
tetramethylolmethane tetramethacrylate,
trimethylolpropane triacrylate,
trimethylolpropane trimethacrylate,
trimethylolethane triacrylate,
trimethylolethane trimethacrylate,
dipentaerythritol hexaacrylate, and
dipentaerythritol hexamethacrylate

2. Polyfunctional monomers having an alcoholic hydroxyl group
Tetramethylolmethane triacrylate,
tetramethylolmethane trimethacrylate,
tetramethylolmethane diacrylate,
tetramethylolmethane dimethacrylate,
dipentaerythritol di- to penta-(meth)acrylate, and epoxy esters of the formula

($R_1$ = H or $CH_3$; and R = $C_2H_4$, $C_6H_{12}$, —CH$_2$—C(CH$_3$)$_2$—CH$_2$—, etc.), such as polyethylene glycol diglycidyl ether di(meth)acrylate $(3 \geq n \geq 1; R_1 = H, CH_3$ polypropylene glycol diglycidyl ether di(meth)acrylate ($R_1$ = H, $CH_3$; n = 1–24)

glycerol tri(meth)acrylate, or glycerol di(meth)acrylate.

3. Polyfunctional monomers having an oxyalkylene group:
Polyethylene glycol di(meth)acrylate of the formula

($R_1$ = H, $CH_3$; $3 \geq n \geq 1$)

polypropylene glycol di(meth)acrylate of the formula ($R_1$ = H or —$CH_3$; n = 1–24)

1,3-butylene glycol di(meth)acrylate,
1,4-butylene glycol di(meth)acrylate,
neopentyl glycol di(meth)acrylate,
2,2'-bis[4-(meth)acryloxydiethoxyphenyl]oropane of the formula ($R_1$ = H or —$CH_3$)

2,2'-bis[4-(meth)acryloxy-propoxyphenyl]propane.

4. Monomers having a hydrophilic group:
Epoxy ester (meth)acrylic acid adducts of the formula

($R_1$ = H or —$CH_3$)

N,N-dimethyl (meth)acrylamide,
diacetone (meth)acrylamide,
alkoxymethyl(meth)acrylamides of the formula

($R_1$ = H or —$CH_3$; $R_2$ = $C_1$-$C_{20}$ alkyl)

ethylenebisacrylamide,
hydroxyalkyl (meth)acrylates of the formula (R = alkylene; $R_1$ = H or —$CH_3$)

vinyl ethers of the formula $CH_2$=CHOR (R=H, —$CH_3$)

vinyl acetates of the formula $CH_2$=CHCOOR (R=alkyl)

vinyl cyanoacetate,
vinyl salicylate,
methoxypolyethylene glycol (meth)acrylate of the formula

($R_1$ = H or —$CH_3$; 3 ≧ n), glycidyl (meth)acrylate,
vinylpyridine, and
glycerol mono(meth)acrylate.

The aforesaid synthetic polymer can also be prepared by copolymerizing a monomeric mixture composed of a monomer having a non-dissociable hydrophilic group and a monomer having a hydrophobic group in suitable proportions.

Examples of the monomer having a non-dissociable hydrophilic group are listed below.

1. Polyfunctional group having an alcoholic hydroxyl group:
Polyethylene glycol diglycidyl ether di(meth)acrylate of the formula given hereinabove,
glycerin diglycidyl ether di(meth)acrylate ($R_1$ = H, —$CH_3$)

2. Polyfunctional monomers having an oxyalkylene group:

Alkylene glycol di(meth)acrylates of the formula

($R_1$ = H or —$CH_3$; R = alkylene)

polyethylene glycol di(meth)acrylate of the formula ($R_1$ = H or —$CH_3$; n ≧ 3)

3. Monomers having a hydrophilic group:
Methacrylamide, 2-hydroxyethyl (meth)acrylate, acrylonitrile, and methoxypolyethylene glycol (meth)acrylate of the formula ($R_1$ = H or —$CH_3$; n ≧ 3).

Examples of the monomer having a hydrophobic group include divinylbenzene, diallyl phthalate, triallyl cyanurate, triallyl isocyanurate, triacryl formal, vinyl esters of fatty acids represented by the formula RCOOCH=$CH_2$ (in which RCOO is a residue of propionic acid, butyric acid, caproic acid, stearic acid, acrylic acid, methacrylic acid, crotonic acid, sorbic acid, benzoic acid, etc.), alkyl (meth)acrylates, styrene and its derivatives (e.g., α-methylstyrene, ethylstyrene, p-cyanostyrene or 2,5-dihydroxystyrene), N-vinyl carbazole, methyl vinyl ketone, and vinyl naphthalene.

In the synthetic polymer, the non-dissociable hydrophilic groups and the hydrophobic groups should be present in properly balanced proportions. For example if n is more than 3 in polyethylene glycol dimethacrylate of the formula the proportion of oxyethylene groups (O$CH_2$$CH_2$) which are hydrophilic becomes larger than the proportion of the methyl and methylene groups which are hydrophobic. Thus, a filler comprising a synthetic polymer obtained by polymerizing this monomer exhibits only very weak hydrophobic interaction. Only when n in the above formula is from 1 to 3 (3 ≧ n ≧ 1), the resulting filler shows satisfactory hydrophobic interaction.

The polymerization is performed preferably by an aqueous suspension polymerization method. Polymers having a diameter of 5 to 200 microns can be obtained by adding a polymerization catalyst and a suspension stabilizer to a monomer having both a non-dissociable hydrophilic group and a hydrophobic group or a monomeric mixture in predetermined proportions of monomers having these groups separately, and polymerizing the monomer or monomeric mixture in aqueous suspension with stirring. Known polymerization procedures can be used in the aqueous suspension polymerization. If the polymerization is carried out in the presence of an organic solvent capable of dissolving such monomers but incapable of dissolving the resulting polymer, the resulting polymer particles become porous and increase in surface area. A filler comprising such a polymer is effective for increasing its separating efficiency.

The filler for high-speed liquid chromatography is required to have high mechanical strength and reduced swellability. Desirably, therefore, the filler is in the form of spherical particles and also is crosslinked. Accordingly, at least one of the non-dissociable hydrophilic group and the hydrophobic group is desirably polyfunctional.

The polymer particles obtained by polymerization are dried by heating, etc. The dried particles are dispersed in water to determine whether they become wet with water. Those particles which do not become wet with water cannot be used in liquid chromatography involving use of water as an eluent and thus cannot be the filler of this invention. Fine particles and coarse particles are removed from the polymer particles, and the resulting polymer particles of a specified particle diameter are packed into a column for liquid chromatography. The eluting behavior of the polymer particles is observed, for example, by charging polyethylene glycol having a molecular weight of 400 (PET 400; polyethylene glycol having an average degree of polymerization of 8 but containing components having degrees of polymerization of 4 to 15) into the column and eluting the column with deionized water as an eluent. In order for such polymer particles to be usable as the filler of this invention, it is necessary that in chromatography at room temperature and a higher temperature (e.g., 50° C.), the elution time of the sample polyethylene glycol at the higher temperature is longer than that at room temperature.

The synthetic polymer selected by the aforesaid two testing methods can be used as a filler for liquid chromatography in accordance with this invention which has both excellent hydrophilicity and excellent hydrophobic interaction.

The liquid-chromatographic filler of this invention described hereinabove permits separation of hydrophilic substances with good accuracy using an aqueous medium as an eluent. Accordingly, it exhibits especially good performance in separating biochemical substances, particularly serum proteins, enzymes, vitamins and amino acids.

The present invention also pertains to a method for separating water-soluble substances, particularly hydrophilic biochemical substances, using the filler described hereinabove.

For example, it is very important from the viewpoint of medical therapy to fractionate proteins contained in the plasma into highly pure fractions. For fractionation of plasma proteins, a procedure of precipitation and fractionation by addition of ethanol is in widespread use. Such a method, however, has various defects. For example, ethanol tends to remain in the fractions obtained. Since structurally similar plasma proteins are difficult to separate from each other, it is difficult to increase the purity of a given component. Furthermore, since a long period of time is required for classification, the protein samples are likely to undergo spoilage and denaturation during such a time.

Accordingly, it is another object of this invention to provide a method for separating water-soluble substances, which is free from these defects.

The present invention thus provides a method for separating water-soluble substances which comprises subjecting said water-soluble substances to liquid chromatography using an aqueous medium as an eluent and a filler comprising a particulate synthetic polymer, said filler exhibiting such a behavior that in chromatography using polyethylene glycol as a sample and water as an eluent, the elution time of the sample increases with a rise in temperature.

The present invention also provides a method for separating water-soluble substances in the aforesaid manner, in which pH of the eluent is varied at the time of separating the water-soluble substances.

Furthermore, the present invention provides a method for separating water-soluble substances, which comprises subjecting the water-soluble substances to liquid chromatography using a filler comprising a particulate synthetic polymer having both a non-dissociable hydrophilic group and a hydrophobic group in the molecule, and an aqueous medium, particularly water whose pH has been adjusted with various buffers, as an eluent, characterized in that the pH of the eluent is varied as the chromatography proceeds.

The aqueous medium denotes pure water, water containing inorganic salts or an aqueous solution substantially free from an organic solvent.

As stated hereinabove, the filler of this invention permits effective separation of hydrophilic biochemical substances, especially water-soluble substances, by liquid chromatography using an aqueous medium as an eluent. It has now been found that varying of the pH of the aforesaid eluent is effective. Specifically, it has been found that a component which cannot be separated fully by liquid chromatography while the pH of the eluent is maintained constant can be surely separated by properly varying the pH of the eluent during chromatography.

Generally, the pH of the eluent is varied preferably by changing the composition of the eluent using a buffer. Suitable buffers include, for example, an aqueous solution of acetic acid and sodium acetate, an aqueous solution of phosphoric acid and dipotassium phosphate, and an aqueous solution of citric acid and sodium citrate.

The manner of varying the pH of the eluent is not particularly limited. Generally, however, it is preferred to increase the pH, for example to change the pH from the acidic side to weak acidity (e.g., pH 6) to weak alkalinity (e.g., pH 8). The rate of varying the pH may range from a slow rate to a rapid rate depending upon the type of a sample to be separated or the purpose of separation. For example, when serum proteins are eluted while gradually increasing the pH of the eluent from 3, $\gamma$-globulin comes out most early. Then, $\alpha$-globulin is eluted, followed by albumin and $\beta$-globulin.

Addition of a salt such as sodium chloride or ammonium sulfate at this time promotes elution, and raising the temperature generally retards elution. Furthermore, elution of proteins is generally promoted by adding up to 10% by weight of an organic solvent such as methanol or acetone. These means may be employed as required.

Since according to the separating method of this invention, the separation is carried out by liquid chromatography while varying the pH of the eluent, water-soluble substances which are generally considered difficult to separate can be separated conveniently, and rapidly with good accuracy. The method of this invention is effective particularly for separation of hydrophilic biochemical substances such as plasma proteins, amino acids and enzymes.

The following Examples illustrate the present invention more specifically.

EXAMPLE 1

A 2-liter separable flask equipped with a condenser, a stirrer, a thermometer and a dropping funnel was charged with a mixture of 400 ml of a 4% by weight aqueous solution of polyvinyl alcohol, 100 g of tetramethylolmethane triacrylate and 1.5 g of benzoyl peroxide. The mixture was heated to 80° C. with stirring at 400 rpm, and reacted at this temperature for 10 hours. The product was cooled. After cooling, the polymerization product was separated from the mother liquor, and washed with hot water and acetone to afford a spherical polymer having a particle diameter of 5 to 20 microns. The resulting particulate polymer was found to be fully wettable with water. Fine particles and coarse particles were removed, and the resulting polymer particles having a particle diameter of 8 to 12 microns were dispersed in 800 ml of deionized water. The dispersion was fed under pressure into a stainless steel column (diameter 7.9 mm, length 50 cm) at a rate of 1.6 ml/min. using a high-pressure fixed flow rate pump.

Figure 1:
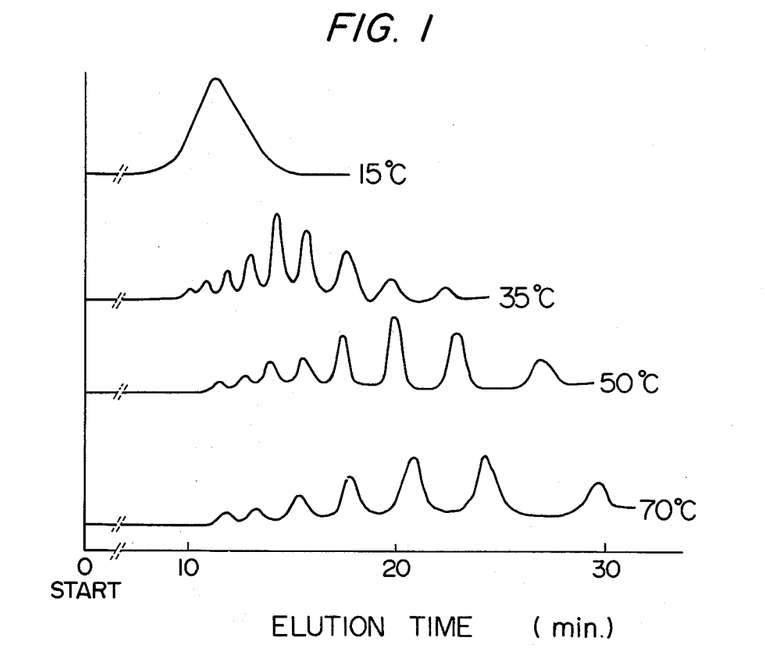
FIG. 1 shows chromatograms obtained in Example 1 at varying temperatures.

The packed column was connected to a high-speed liquid chromatographic device (High-speed Liquid chromatograph Model 830, a product of Shimazu-Du Pont). Polyethylene glycol (PEG 400; a product of Wako Pure Chemical Co., Ltd.) as a sample was chromatographed on the packed column using deionized water as an eluent while maintaining the temperature of the column at 15° C., 35° C., 50° C. and 70° C., respectively. The chromatograms obtained at these temperatures are shown in FIG. 1 of the accompanying drawings. It is seen that the elution times of the individual ingredients having different degrees of polymerization increased at higher temperatures, and that at 50° C., the individual components were separated most clearly.

EXAMPLE 2

The same polymerization as in Example 1 was performed except that 40 g of hydroxymethyl methacrylate and 30 g of styrene were used as the monomers. The resulting spherical polymer having a particle diameter of 5 to 15 microns was packed into a stainless steel column in the same way as in Example 1.

The resulting packed column had good affinity with water. The packed column was connected to the same high-speed chromatographic device as used in Example 1, and the same polyethylene glycol sample as used in Example 1 was chromatographed on the packed column using deionized water as an eluent while maintaining the column temperature at 20° C. and 50° C., respectively. It is seen that the elution times of the individual ingredients having different degrees of polymerization increased at 50° C. Specifically, the elution time of a component having a degree of polymerization of 8 was 12 minutes at 20° C., and 32 minutes at 50° C.

EXAMPLE 3

The same polymerization apparatus as used in Example 1 was charged with a mixture of 400 ml of a 4% by weight aqueous solution of polyvinyl alcohol, 50 g of tetramethylolmethane triacrylate, 50 g of neopentyl glycol dimethacrylate, 100 g of toluene and 1.5 g of benzoyl peroxide. The mixture was heated to 75° C. with stirring at 400 rpm, and polymerized at this temperature for 10 hours. The product was cooled, and separated from the mother liquor. The separated polymerization product was washed with hot water and acetone to afford a spherical porous polymer having a particle diameter of 5 to 25 microns. The resulting polymer was found to be well wettable with water. Fine and coarse particles were removed, and the resulting polymer particles having a particle diameter of 10 to 15 microns were dispersed in 100 ml of deionized water. The dispersion was fed into a stainless steel column (7.9 mm in diameter, and 50 cm in length) at a rate of 2.0 ml/min. by means of a high-pressure fixed flow rate pump.

The packed column was connected to the same high-speed liquid-chromatographic device as used in Example 1, and the same polyethylene glycol as a sample was chromatographed on the packed column using deionized water as an eluent while maintaining the temperature of the column at room temperature and 50° C., respectively. The elution times of the individual components at 50° C. were longer than those at room temperature.

EXAMPLE 4

Amino acids were separated using the filler produced in Example 1.

The separating conditions were as follows:
Eluent: 1/20 M acetic acid-sodium acetate buffer adjusted to pH 3.4.
Detector: differential refractometer
Temperature: 45° C.
Flow rate of the eluent: 1.0 ml/min.
Sample: a mixture of alanine, leucine, phenylalanine and tyrosine.

Figure 2:
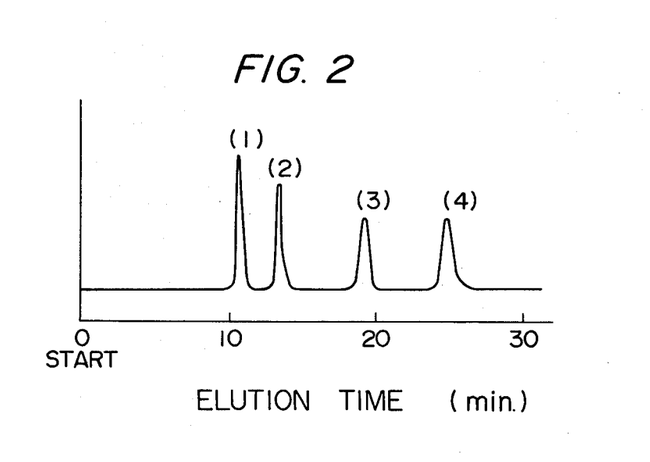
FIG. 2 is a chromatogram obtained in Example 4 in which (1) refers to alanine; (2) to leucine; (3) to tyrosine and (4) to phenylalanine.

The resulting chromatogram was as shown in FIG. 2. In FIG. 2, (1), (2), (3) and (4) respectively show peaks of alanine, leucine, tyrosine, and phenylalanine.

EXAMPLE 5

The filler produced in Example 1 was packed in the high-speed liquid-chromatographic column in the same way as in Example 1. While maintaining the temperature of the column at 25° C., serum proteins were fractionated in the following manner.

Figure 3:
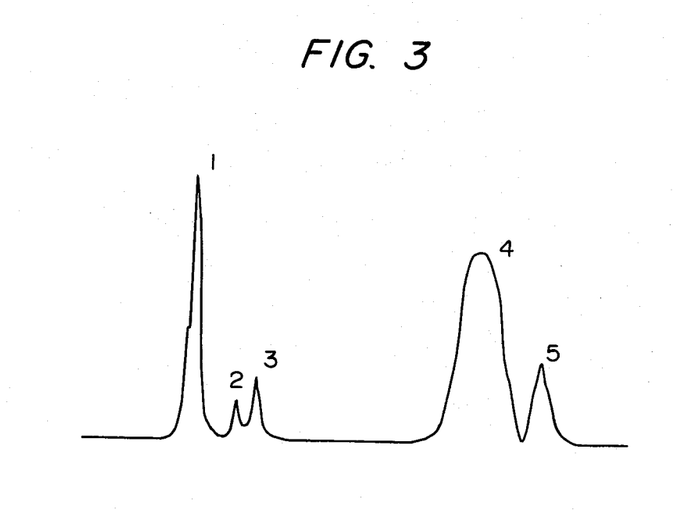
FIG. 3 is a chromatogram obtained in Example 5, in which 1 to 5 show peaks of the eluted components.

Standard serum (100 microliters) was injected into the column using a microsyringe. The column was eluted with a mixture of 0.1 N acetic acid and 0.1 N sodium acetate in varying ratios as an eluent. Specifically, the elution was started at a pH of 3.0, and the proportions of the two solutions in the mixture were adjusted so that the pH of the mixture changed at a rate of 1 per 5 minutes. After the pH of the eluent reached 7.0, the elution was continued without varying the composition of the eluent. The resulting chromatogram is shown in FIG. 3. In this chromatogram, ultraviolet light of wavelength 280 nm was used as a detector.

Components corresponding to the main peaks 1 to 5 in FIG. 1 were separated and concentrated, and then subjected to electrophoresis in a customary manner using a support composed of a cellulose acetate membrane to identify the individual components. It was determined that the components 1, 2 and 3 were γ-globulin; the component 4, a mixture of albumin and α-globulin; and the component 5, β-globulin. the components 1, 2, 3 and 5 were found to be completely free from other substances, and the separating performance of the column was very good.

In order to determine the percent recovery in the above eluting procedure, the components corresponding to peaks 1 to 5 were not separated but recovered in lump. The absorbance of the recovered product was compared with that of the standard serum, and the total percent recovery of proteins was determined. The percent recovery was found to be more than 95%.

EXAMPLE 6

A spherical polymer was produced under the same polymerization conditions as in Example 1 except that 100 g of diethylene glycol diacrylate was used instead of the tetramethylolmethane triacrylate. The polymer particles were classified, and packed in the same way as in Example 1. Using the same device as used in Example 5, the component 4 obtained in Example 5 was separated.

The component 4 was injected into the column, and the column was eluted with a mixture of phosphoric acid and dipotassium phosphate (0.1 mole/liter) while varying the pH of the eluent from 5.0 to 8.0 at a rate of 1 per 10 minutes. The resulting chromatogram contained two peaks. It was ascertained by electrophoresis in the same way as in Example 5 that the fraction having a shorter elution time was α-globulin, and the fraction having a longer elution time was albumin.

EXAMPLE 7

A porous spherical polymer was produced under the same polymerization conditions except that 50 g of hydroxyethyl methacrylate and 50 g of tetramethylolmethane triacrylate were used as the monomers and 80 g of toluene was added for rendering the resulting polymer particles porous. The resulting polymer particlers were classified, and packed in the same way as in Example 1. Using the same apparatus as in Example 5, the following separating procedure was performed.

Blood cell components were removed from fresh blood in a customary manner. The resulting plasma (100 microliters) was injected into the column by a microsyringe. The column was eluted at room temperature with a citric acid-sodium citrate (0.05 mole/liter) buffer while varying the pH of the eluent continuously from 3.0 to 6.0 at a rate of about 1 per minute. The resulting chromatogram was nearly the same as that obtained in Example 5, but a new peak appeared between the peaks 3 and 4. A component corresponding to the new peak was separated and concentrated, and qualitatively analyzed by electrophoresis. This component corresponded to the site of fibrinogen.

EXAMPLE 8

Serum (100 microliters) was charged on the same column as used in Example 7, and the column was eluted with acetic acid/sodium acetate (0.2 mole/liter) buffer at pH 3.6 without changing the pH of the eluent. The eluate was only γ-globulin. When the column was further eluted with the same eluent but having a pH of 6.0, other serum components were separated.

This procedure is an efficient method for selectively separating large amounts of γ-globulin alone in concentrated form, and has a high commercial value.

EXAMPLE 9

Using the same high-speed liquid-chromatographic column as used in Example 5, the following separating procedure was performed.

A mixture of *L-dopa* (component 1), *L-noradrenaline* (component 2), and *L-adrenaline* (component 3), catecholamine derivatives, was injected into the column, and the column was eluted with 0.1 N acetic acid-sodium acetate buffer (pH adjusted to 6.0 and 2.9, respectively) as an eluent. When at this time, the pH of the eluent was continuously varied from 2.9 to 6.0 by the gradient elution method at a rate of 0.5 per minute, two peaks were recognized. The first peak corresponded to a mixture of components 1 and 2, and the second peak, to component 3.

When the rate of varying the pH was changed to 0.1 per minute three peaks appeared. The first peak corresponded to component 2; the second peak, to component 1; and the third peak, to component 3.

EXAMPLE 10

Glucose oxidase was chromatographically purified using the filler obtained in Example 2.

The conditions were as follows:
Eluent: phosphate buffer whose pH was varied from 6.0 to 8.0; developed by the gradient method
Detector: ultraviolet light detector (280 nm)
Temperature: 40° C.
Flow rate of the eluent: 1.0 ml/min.
Sample: Crude glucose oxidase (yellow powder)

The chromatogram obtained showed three peaks whose areas were 1:1.3:3.8 in the order of elution. The eluates corresponding to the three peaks were separated, and their enzyme activities were determined by the p-oxidase indamine dye method. Only the fraction corresponding to the last-eluted peak showed enzyme activity.

Accordingly, the present filler can be used effectively for purification of enzymes.

EXAMPLE 11

Main proteins in human serum were separated by using the filler produced in Example 3.

The results were as follows:
Eluent: Acetate buffer whose pH was varied from 4.0 to 6.0; developed by the gradient elution method.
Detector: Ultraviolet light detector (280 nm)
Temperature: 20° C.
Flow rate of the eluent: 1.0 ml/min.
Sample: human serum albumin and human serum γ-globulin.

The resulting chromatogram contained two peaks. By identification using an authentic sample, it was determined that these peaks corresponded to γ-globulin and albumin eluted in this order.

EXAMPLE 12

Caffeine and its analogs, i.e. xanthine and theophylline, were separated using the same filler and device as used in Example 11. An ammonia/ammonium chloride buffer was used as an eluent, and the elution was carried out at a pH of 9.5. Only xanthine could be eluted, while the other components remained unseparated.

Then, by the gradient elution method, the pH was continuously varied from 9.5 to 6.8 (at a rate of 0.1 per minute). As a result, three peaks appeared, which corresponded respectively to xanthine, theophilline and caffeine in the increasing order of the elution time.

Comparative Example 1

A commercially available GPC hydrophobic filler comprising a porous resin of the styrene/divinylbenzene type (HSG60, a tradename for a product of Shimazu Seisakusho) was packed into a column, and the column was connected to the same high-speed liquid-chromatographic device as used in Example 1. When water was introduced under pressure into the column, no liquid flowed out of the column even when the pressure at the inlet of the column reached 100 kg/cm$^2$. Thus, this column could not be used for gel permeation chromatography using water as an eluent.

Comparative Example 2

A polymer was prepared under the same conditions as in Example 1 except that tetraethylene glycol dimethacrylate was used as the monomer. Fine and coarse particles were removed, and the resulting polymer particles having a particle diameter of 10 to 15 microns were packed into the same stainless steel column as used in Example 1. The packed column was connected to the same high-speed liquid-chromatographic device as used in Example 1, and the same polyethylene glycol was used in Example 1 was chromatographed using deionized water as an eluent while maintaining the temperature of the column at room temperature and 50° C. respectively. The resulting chromatogram showed that there was hardly any difference in elution time between the elution at room temperature and that at 50° C. The elution time of the sample at 50° C. did not become longer than that at room temperature, and the sample was not separated into its components.

The present filler showed only very weak hydrophobic interaction, and therefore is unsuitable for separation of biochemical substances.

For example, when the separation was carried out in the same way as in Example 11 using this filler, the two components were eluted without being held by the filler. Thus, separation of the two components with this filler was impossible.

What we claim is:

1. A method for separating water-soluble substances, which comprises subjecting said water-soluble substances to reversed phase liquid chromatography using an aqueous medium as an eluent and a filler comprising a particulate synthetic polymer, said polymer being a single polymer of (a) a monomer selected from the group consisting of tetramethylolmethane di-, tri- or tetra-(meth)acrylate, trimethylolpropane tri-(meth)acrylate, trimethylolethane tri-(meth) acrylate, dipentaerythritol di- to hexa-(meth)acrylate, glycerol di- or tri-(meth)acrylate, polyethylene glycol di-(meth)acrylate of the formula wherein R$_1$ is H or CH$_3$, and $3 \geq n \geq 1$, polypropylene glycol di-(meth)acrylate of the formula wherein R$_1$ is H or CH$_3$, and n is an integer of 1-24, and neopentyl glycol di(meth)acrylate, or (b) a combination of two or more of said monomers, said filler exhibiting a behavior such that in liquid chromatography using polyethylene glycol as a sample and water as an eluent, the elution time of the sample increases with a rise in temperature.

2. The method of claim 1 wherein the pH of the aqueous medium as eluent is varied during chromatography.

3. The method of claim 1 wherein the pH of the aqueous medium as eluent is increased as the chromatography proceeds.

4. The method of claim 1 wherein said water-soluble substances are hydrophilic biochemical substances.

5. The method of claim 1 wherein said water-soluble substances are proteins, enzymes, vitamins or amino acids.

* * * * *

UNITED STATES PATENT AND TRADEMARK OFFICE
CERTIFICATE OF CORRECTION

PATENT NO. : 4,447,328
DATED : May 8, 1984
INVENTOR(S) : Fumio KAMIYAMA, Kazutoshi YAMAZAKI, Minoru KOHARA and Mituo NAGATA It is certified that error appears in the above—identified patent and that said Letters Patent is hereby corrected as shown below:

In the heading of the Patent, correct the name of the Assignee to read as: --SEKISUI KAGAKU KOGYO KABUSHIKI KAISHA--.

Signed and Sealed this

Eighteenth Day of December 1984

[SEAL]

Attest:

Attesting Officer

GERALD J. MOSSINGHOFF

Commissioner of Patents and Trademarks